(12) United States Patent
Manzo et al.

(10) Patent No.: US 8,575,224 B2
(45) Date of Patent: Nov. 5, 2013

(54) PROCEDURE FOR OBTAINING AN AQUEOUS DISPERSION OF ALCOHOLS AND ACIDS FROM JOJOBA OIL, PROCESSES FOR OBTAINING SELF-EMULSIFIED JOJOBA OIL, AQUEOUS DISPERSIONS AND EMULSIONS OF JOJOBA OIL IN THE SAME AND PHARMACEUTICAL OR COSMETIC COMPOSITIONS COMPRISING THE SAME

(75) Inventors: Rubén Hilario Manzo, Córdoba (AR); Norma Graciela Maggia, Córdoba (AR)

(73) Assignees: G.S.P. Emprendimientos Agropecuarios Sociedad Anonima, La Rioja, Provincia de la Rioja (AR); Universidad Nacional de Cordoba, Cordoba, Provincia de Cordoba (AR)

( * ) Notice: Subject to any disclaimer, the term of this patent is extended or adjusted under 35 U.S.C. 154(b) by 109 days.

(21) Appl. No.: 13/064,715

(22) Filed: Apr. 11, 2011

(65) Prior Publication Data

US 2011/0294765 A1 Dec. 1, 2011

(30) Foreign Application Priority Data

Jun. 1, 2010 (AR) .............................. P20100101915

(51) Int. Cl.
*A61K 31/23* (2006.01)
(52) U.S. Cl.
USPC .......................................... 514/784; 514/552
(58) Field of Classification Search
USPC ........... 554/124, 156, 158, 195; 514/552, 784
See application file for complete search history.

(56) References Cited

U.S. PATENT DOCUMENTS

| 6,559,182 | B1 | 5/2003 | Purcell |
| 7,435,424 | B1 | 10/2008 | Copeland et al. |
| 2003/0008022 | A1 | 1/2003 | Mogy |

FOREIGN PATENT DOCUMENTS

| IN | 178981 | * | 8/1997 | ................ C11C 1/04 |
| IN | 179013 | * | 8/1997 | ................ C11C 1/04 |
| WO | 03049674 | | 6/2003 | |
| WO | 2006112938 | | 10/2006 | |

OTHER PUBLICATIONS

Miwa, T.K., et al., Jojoba oil wax esters and derived fatty acids and aocohols: Gas ghromatographic analysis, 1971, Journal of the American Oil Chemists' Society, vol. 48, No. 6, pp. 259-264.*

* cited by examiner

*Primary Examiner* — Yate K Cutliff
(74) *Attorney, Agent, or Firm* — MH2 Technology Law Group, LLP

(57) ABSTRACT

Processes for obtaining aqueous dispersions comprising alcohols and acids obtained by hydrolysis of jojoba oil. Hydrolyzed jojoba oil products are treated by a process comprising neutralization of jojoba fatty acids with aliphatic organic amines dissolved in a co-solvent followed by the dispersion of both the neutralized fatty acids together with jojoba alcohols in an aqueous medium. The products obtained, generically named hydrolyzed jojoba oil (HJO), promote transdermal absorption and are useful vehicles for carrying a wide range of pharmaceutical and cosmetic compositions, including pharmaceutical and cosmetic compositions comprising either lipophilic or hydrophilic active principles. The HJO can also be used to produce a semisolid, self-emulsified jojoba oil (SEJO), obtained by emulsifying the HJO in jojoba oil.

15 Claims, 5 Drawing Sheets

PROCEDURE FOR OBTAINING AN AQUEOUS DISPERSION OF ALCOHOLS AND ACIDS FROM JOJOBA OIL, PROCESSES FOR OBTAINING SELF-EMULSIFIED JOJOBA OIL, AQUEOUS DISPERSIONS AND EMULSIONS OF JOJOBA OIL IN THE SAME AND PHARMACEUTICAL OR COSMETIC COMPOSITIONS COMPRISING THE SAME

CROSS-REFERENCE TO RELATED APPLICATION

The present application claims the benefit of Argentine Patent Application No. 20100101915 filed on 1 Jun. 2010, the entire disclosure of which is hereby incorporated herein by reference in its entirety.

FIELD OF THE INVENTION

The present invention relates to the field of vehicles used in pharmacy and cosmetic industries as carriers of active compounds, especially those vehicles based on natural vegetable oils and, more specifically, those based on jojoba oil.

DESCRIPTION OF THE BACKGROUND ART

Jojoba oil is obtained from the seed of Simmondsia Chinensis, which contains about 50% by weight of this oil, and which on account of its chemical structure is not a fat but a liquid wax.

This liquid wax is made of a mixture of straight chain monounsaturated fatty acid esters from 20 to 22 carbon atoms and homologous alcohols most of the same size, with an average chain length from 40 to 42 carbon atoms having one unsaturated hydrocarbon on each side of the ester bond (Wisniak, Jaime, The chemistry and technology of jojoba oil. American Oil Chemists Society, USA 1987). Its general formula is as follows:

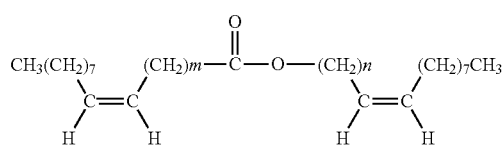

The unsaturated acids with the highest presence are eicosanoic acid (of 20 carbon atoms, C20), docosanoic acid (C22), with lower amounts of oleic acid (C18). Alcohols are mostly docosanoic alcohol and eicosanoic alcohol (Wisniak, Jaime, The chemistry and technology of jojoba oil. American Oil Chemists Society, USA 1987).

The intensive studies conducted and its use for more than 30 years in cosmetic products, show that jojoba oil is not toxic when it is applied on the human skin, or administered orally to mice, rats, marmots and rabbits (Verbiscar, Anthony; WO99/62451—Topical transdermal treatment).

Jojoba oil has been effectively used to treat different skin disorders together with other therapeutic agents, for example salicylic acid in the treatment of psoriasis, dandruff, acne and skin flaking. It is effective with zinc oxide in the treatment of contact dermatitis, cutaneous rash and allergic dermatitis. It is also effectively used for treating insect bites or fungal foot infections, as well as for treating first degree burns and sun burns, being a good protector against ultraviolet radiation during exposure to sun.

It is a first selection for treating wounds, even those associated with inflammatory processes and scars. It has been used as an auxiliary agent for the treatment of alopecia.

Jojoba oil is also successfully used for a wide range of disorders such as rheumatic pain and arthritis, otitis, ocular disorders, as well as in suppositories for treating anal fissures, hemorrhoids and non infectious vaginitis (El Mogy, Nabil Sadek; Patent Application US2003/0008022—Medical effect of Jojoba oil).

Jojoba oil esters are effective for promoting quick relief of infected zones or preventing future relapses. Jojoba oil is absorbed through the skin much more easily and quickly than other substances previously used without having to add surfactants or emollients (Purcell, Hal; U.S. Pat. No. 6,559,182 B1 (May 6, 2003), WO 2003/49674—Method of treatment of enveloped viruses using jojoba oil esters).

Jojoba oil can be used as a promoter of the therapeutic efficacy of other active principles, as it increases percutaneous absorption and accumulation in the epidermis, and is able to act as a carrier of the active principles to deep layers of the skin to perform their function. Examples of these active ingredients are anti-inflammatory drugs such as ibuprofen and ketoprofen; antifungal agents such as griseofulvin; liposoluble vitamins such as vitamin A, vitamin D and vitamin E; antineoplastic agents such as Taxol and Paclitaxel; hormonal agents such as testosterone, estrogen, cortisone and prostaglandins; as well as other antiviral agents such as nucleoside and immune response modulator analogue drugs (Purcell, Hal, U.S. Pat. No. 6,559,182 B1 (May 6, 2003), WO2003/49674—Method of treatment of enveloped viruses using jojoba oil esters).

However, jojoba oil itself, used as a vehicle, is only able to dissolve lipophilic active principles, but is not useful as a vehicle of hydrophilic active principles. Therefore, a new vehicle derived from jojoba oil and capable of carrying a wide range of active principles, either lipophilic or hydrophilic ones, and also exhibiting the advantages offered by products whose vehicle is aqueous in relation to the oily ones is desirable.

A composition containing derivative products of hydrolysed jojoba oil was described in U.S. Pat. No. 7,435,424. When this composition is included from 5% to 10% in other cosmetics, repellent or pesticides products, it increases the persistence of those products over an animal's skin or hair. In spite of this composition it is not itself an aqueous carrier that produces the dissolution of cosmetics or pharmaceuticals active principles, either lipophilics or hydrophilics.

An important field wherein the use of jojoba oil is also effective is the prevention and treatment of infections by virus such as herpes viruses, including but not limited to, Herpes simplex virus (HSV) type 1, mostly associated to facial infections on lips, mouth, nose and eyes; HSV type 2, mostly genital; varicella zoster virus also known as human herpes virus (HHV) type 3; HHV type 8, associated with Kaposi's sarcoma.

In this respect, it has been found that alcohols with a chain length from 16 to 20 carbons and at least one unsaturated carbon are effective in inhibiting replication of viruses with lipid coating in cell cultures; numerous studies have shown the antiviral activity of n-docosanol, and several patents support these publications (Verbiscar, Anthony; WO 2006/112938A1—Formulations useful for the treatment of varicella zoster virus infections and methods for the use thereof).

However, jojoba oil does not contain alcohols in free form but rather in esterified form. Therefore it is desirable to have a jojoba oil vehicle comprising the free alcohols which, considering their structural characteristics, are per se an active principle against lipid coated viruses.

SUMMARY OF THE INVENTION

Aqueous dispersions comprised of alcohols and acids obtained by hydrolysis of jojoba oil were developed.

Hydrolyzed jojoba oil products are treated by a process comprising neutralization of jojoba fatty acids with aliphatic organic amines dissolved in a co-solvent followed by the dispersion of both the neutralized fatty acids together with jojoba alcohols in an aqueous medium.

The products obtained named generically hydrolyzed jojoba oil (hereinafter HJO) are presented as high-viscosity, transparent, translucent or opaque, physically stable dispersions with a pH between 7.00 and 8.50.

The HJO is capable of carrying a wide range of pharmaceutical and cosmetic, either hydrophilic or lipophilic, active principles, preferably non-steroidal anti-inflammatory (NSAIDs), local anesthetics, antiviral and antifungal drugs, showing an important effect of promoting transdermal absorption.

The HJO remarkably broadens capacity and usefulness as a pharmaceutical and cosmetic vehicle compared to jojoba oil.

The HJO has the ability of emulsifying jojoba oil producing a semisolid product of bright texture named self-emulsified jojoba oil (hereinafter SEJO) useful as a skin-care cream. The SEJO is capable of carrying liposoluble and hydro soluble vitamins and other active principles of cosmetic use.

DETAILED DESCRIPTION OF THE INVENTION

Procedure

Figure 1:
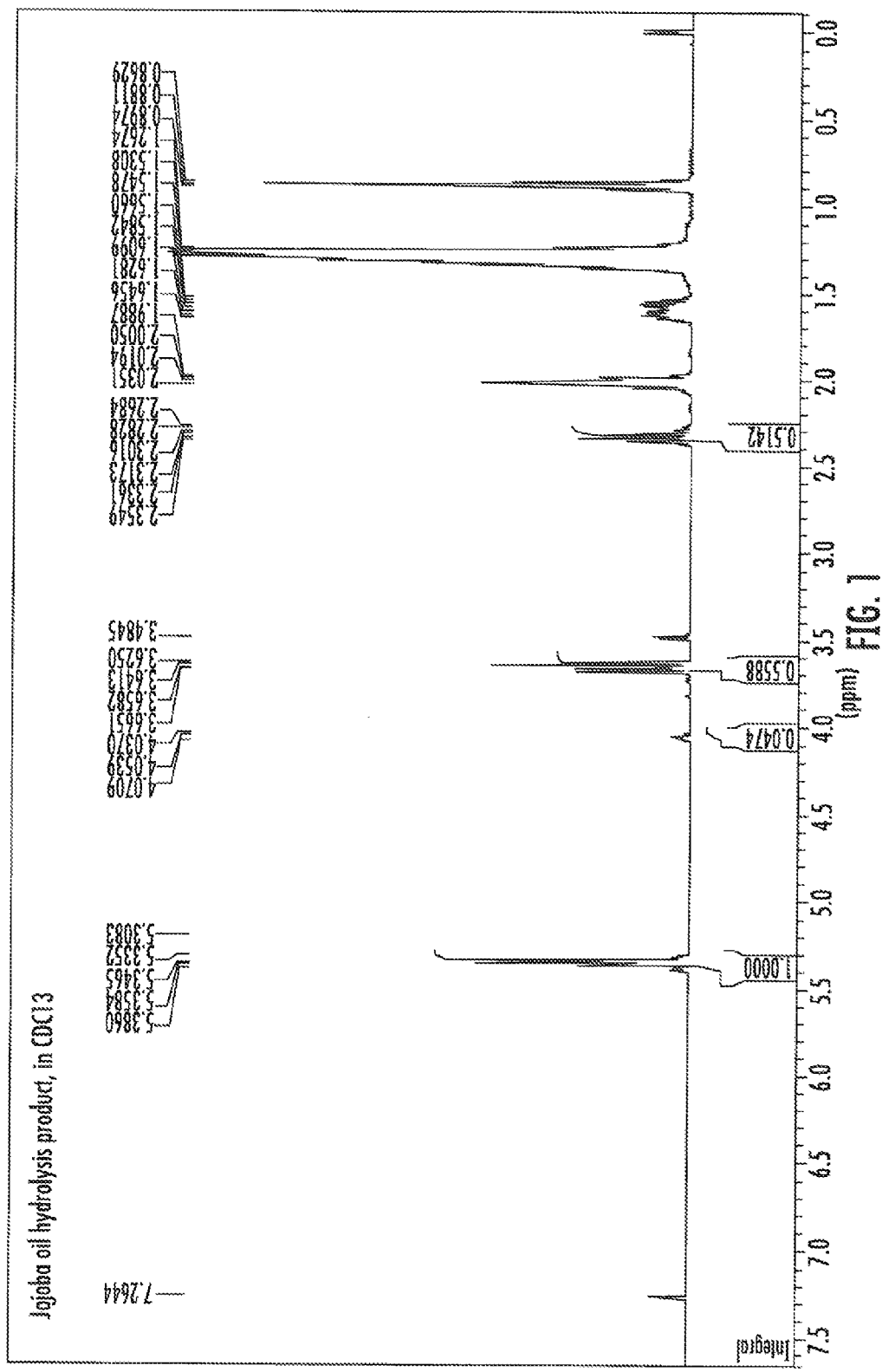
FIG. 1 shows the characterization of the hydrolysis products of Jojoba oil by $^1$H-NMR. The assignments of main signals shows the disappearance of the original product (disappearance of the signals HC—COO—CH $\delta$=4.1 ppm characteristic of Jojoba oil ester group), and the presence of carboxylic acids (—HC—COOH, d=2.3 ppm) and the presence of alcohols (HC—OH, d=3.6 ppm) derived from jojoba wax in equal amounts in relation with the whole mass.

Therefore, one embodiment of the invention is to provide a process for obtaining an aqueous dispersion of alcohols and salified acids from jojoba oil useful as a carrier in pharmaceutical and cosmetic compositions, comprising a first step wherein jojoba oil esters represented by the formula (I) are saponified by treatment with a base (II) to form a mixture of carboxylate (III) and jojoba alcohols (IV):

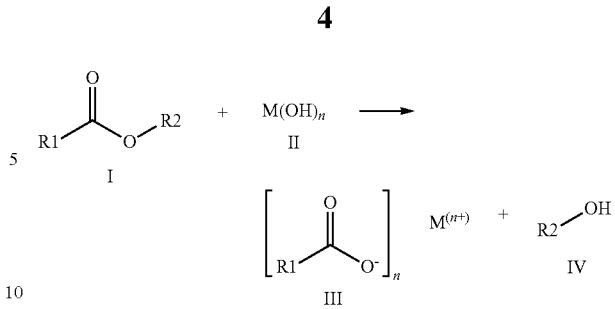

wherein R1 and R2 are alkenes of C20-C22; M is an alkaline metal or alkaline earth metal; and n is 1 or 2.

The base (II) is preferably an alkali metal hydroxide such as lithium hydroxide, sodium hydroxide, potassium hydroxide, or an alkali earth metal such as calcium hydroxide, magnesium hydroxide. More preferably, the base (II) is sodium hydroxide [NaOH] or potassium hydroxide [KOH].

The reaction is conducted in a reaction medium comprising a methyl alcohol:$H_2O$ solution, preferably at a ratio of 99:1, and at boiling temperature, preferably from 60-70° C.

Afterwards, the solvent is evaporated to dryness by means of reduced pressure and the product is treated with an aqueous solution of a strong inorganic acid and/or organic acid in a sufficient amount to neutralize the fatty acid salts and the excess of base present in the reaction medium. Preferably, the inorganic strong acid is hydrochloric acid at concentrations from 1 to 10% w/v.

In this way, the solid or semisolid product obtained comprises mainly a mixture of acids and alcohols of jojoba oil, which are separated from the aqueous medium.

In an alternative procedure prior to solvent evaporation the product is acidified by means of a strong inorganic acid or an organic acid solution to neutralize the fatty acid metallic salts and the excess of base present in the reaction medium. Preferably, the strong inorganic acid is hydrochloric acid at concentrations of 1 to 30% w/v.

The product obtained comprises an upper layer of an oily liquid comprising mainly a mixture of acids and alcohols of jojoba oil and an aqueous layer which may have a precipitated solid comprising the salts resulting from the acidification process. The oily product is recovered and washed by water.

The following step comprises salification of fatty acids, at a ratio from 50 to 100% of the number of existing carboxylic groups by adding the appropriate proportion of an aliphatic organic amine.

Preferably, said aliphatic organic amine is selected from the group consisting of dialkyl ($C_1$-$C_6$) amines, dihydroxyalkyl ($C_1$-$C_6$) amines, trihydroxyalkyl ($C_1$-$C_6$) amines, and mixtures thereof.

More preferably, the aliphatic organic amine used is selected from the group consisting of triethanolamine [(HOCH$_2$CH$_2$)$_3$N], diethanolamine [(HOCH$_2$CH$_2$)$_2$NH], tromethamine [(HOCH$_2$)$_3$CNH$_2$], diethylamine [(CH$_3$CH$_2$)$_2$NH], and mixtures thereof.

The aliphatic organic amine is previously dissolved in a suitable volume of a co-solvent to obtain a co-solvent concentration in the final product from 15% to 25% w/w.

Preferably, the co-solvent is selected from the group consisting of ethyl alcohol [CH$_3$CH$_2$OH], propylene glycol [CH$_3$CHOHCH$_2$OH], and mixtures thereof.

Afterwards the product obtained from salification of the fatty acids by adding the aliphatic organic amine, which also contains the jojoba alcohols and the co-solvent, is dispersed in a sufficient amount of distilled or purified water to obtain a high viscosity product, physically stable at a pH from 7.00 to 8.50 that contains from 15% to 30% weight by weight of the salified product of the hydrolysis of the jojoba oil. This aqueous dispersion we named hydrolyzed jojoba oil (HJO).

Another embodiment of the present invention is a procedure for obtaining self-emulsified jojoba oil (SEJO) containing jojoba oil emulsified in the aqueous dispersion of alcohols and salified acids of hydrolyzed jojoba oil (HJO) according to the preceding discussion. Said procedure comprises the addition of jojoba oil to the hydrolyzed jojoba oil (HJO) at room temperature with vigorously mechanical stirring the mixture, to obtain the self-emulsified jojoba oil product (SEJO) as a semisolid product of homogeneous aspect and bright texture.

Another option for preparing this self-emulsified jojoba oil product (SEJO) involves first contacting the solution comprising the alcohols and fatty acids salified by the aliphatic organic amine dissolved in a co-solvent with the jojoba oil under gently stirring until the complete incorporation of the phases. Afterwards adding water slowly under moderate and constant stirring, to obtain a semisolid product of high viscosity, homogeneous aspect, and bright texture.

Preferably, the self-emulsified jojoba oil (SEJO) contains from 1% to 40% weight by weight of jojoba oil dispersed in the hydrolyzed jojoba oil product (HJO). More preferably, the SEJO contains 15% weight by weight of jojoba oil dispersed in the hydrolyzed jojoba oil product (HJO).

I) Thus, depending on the starting material used, different aqueous dispersions of hydrolyzed jojoba oil can be obtained, preferably the following:

i) Aqueous dispersion of alcohols and salified acids of hydrolyzed jojoba oil (HJO) obtained by treating the fatty acids with triethanolamine in ethanol and dispersed in a sufficient amount of water to obtain a transparent or quasi-transparent product of high viscosity containing from 15% to 30% weight by weight of the salified product of hydrolyzed jojoba oil.

ii) Aqueous dispersion of alcohols and salified acids of hydrolyzed jojoba oil (HJO) obtained by treating the fatty acids with diethanolamine in ethanol and dispersed in a sufficient amount of water to obtain a transparent or quasi-transparent product of high viscosity containing from 15% to 30% weight by weight of the salified product of hydrolyzed jojoba oil.

iii) Aqueous dispersion of alcohols and acids of hydrolyzed jojoba oil (HJO) obtained by treating the fatty acids with diethylamine in ethanol and dispersed in a sufficient amount of water to obtain a transparent or quasi-transparent product of high viscosity containing from 15% to 30% weight by weight of the salified product of hydrolyzed jojoba oil.

iv) Aqueous dispersion of alcohols and salified acids of hydrolyzed jojoba oil (HJO) obtained by treating the fatty acids with tromethamine in ethanol and dispersed in a sufficient amount of water to obtain a transparent or quasi-transparent product of high viscosity containing from 15% to 30% weight by weight of the salified product of hydrolyzed jojoba oil.

v) Aqueous dispersion of alcohols and salified acids of hydrolyzed jojoba oil (HJO) obtained by treating the fatty acids with triethanolamine in propylene glycol and dispersed in a sufficient amount of water to obtain a transparent or quasi-transparent product of high viscosity containing from 15% to 30% weight by weight of the salified product of hydrolyzed jojoba oil.

vi) Aqueous dispersion of alcohols and salified acids of hydrolyzed jojoba oil (HJO) obtained by treating the fatty acids with diethanolamine in propylene glycol and dispersed in a sufficient amount of water to obtain a transparent or quasi-transparent product of high viscosity containing from 15% to 30% weight by weight of the salified product of hydrolyzed jojoba oil.

vii) Aqueous dispersion of alcohols and salified acids of hydrolyzed jojoba oil (HJO) obtained by treating the fatty acids with diethylamine in propylene glycol and dispersed in a sufficient amount of water to obtain a transparent or quasi-transparent product of high viscosity containing from 15% to 30% weight by weight of the salified product of hydrolyzed jojoba oil.

viii) Aqueous dispersion of alcohols and salified acids of hydrolyzed jojoba oil (HJO) obtained by treating the fatty acids with tromethamine in propylene glycol and dispersed in a sufficient amount of water to obtain a transparent or quasi-transparent product of high viscosity containing from 15% to 30% weight by weight of the salified product of hydrolyzed jojoba oil.

ix) Aqueous dispersion of alcohols and salified acids of hydrolyzed jojoba oil (HJO) obtained by treating the fatty acids with triethanolamine in a mixture of ethanol and propylene glycol and dispersed in a sufficient amount of water to obtain a transparent or quasi-transparent product of high viscosity containing from 15% to 30% weight by weight of the salified product of hydrolyzed jojoba oil.

x) Aqueous dispersion of alcohols and salified acids of hydrolyzed jojoba oil (HJO) obtained by treating the fatty acids with diethanolamine in a mixture of ethanol and propylene glycol and dispersed in a sufficient amount of water to obtain a transparent or quasi-transparent product of high viscosity containing from 15% to 30% weight by weight of the salified product of hydrolyzed jojoba oil.

xi) Aqueous dispersion of alcohols and salified acids of hydrolyzed jojoba oil (HJO) obtained by treating the fatty acids with diethylamine in a mixture of ethanol and propylene glycol and dispersed in a sufficient amount of water to obtain a transparent or quasi-transparent product of high viscosity containing from 15% to 30% weight by weight of the salified product of hydrolyzed jojoba oil.

xii) Aqueous dispersion of alcohols and salified acids of hydrolyzed jojoba oil (HJO) obtained by treating the fatty acids with tromethamine in a mixture of ethanol and propylene glycol and dispersed in a sufficient amount of water to obtain a transparent or quasi-transparent product of high viscosity containing from 15% to 30% weight by weight of the salified product of hydrolyzed jojoba oil.

II) Also, from those 12 different salified products of hydrolyzed jojoba oil (HJO) described, it is possible to obtain several self-emulsified jojoba oils (SEJO) by emulsification of jojoba oil in each of them as follows i) Self-emulsified jojoba oil (SEJO) comprising an emulsion from 1% to 40% weight by weight of jojoba oil in HJO obtained by treating the fatty acids with triethanolamine in ethanol and dispersed in a sufficient amount of water to obtain a transparent or quasi-transparent product of high viscosity containing from 15% to 30% weight by weight of the salified product of hydrolyzed jojoba oil.

ii) Self-emulsified jojoba oil (SEJO) comprising an emulsion from 1% to 40% weight by weight of jojoba oil in HJO obtained by treating the fatty acids with diethanolamine in ethanol and dispersed in a sufficient amount of water to obtain a transparent or quasi-transparent product of high viscosity containing from 15% to 30% weight by weight of the salified product of hydrolyzed jojoba oil.

iii) Self-emulsified jojoba oil (SEJO) comprising an emulsion from 1% to 40% weight by weight of jojoba oil in HJO obtained by treating the fatty acids with diethylamine in ethanol and dispersed in a sufficient amount of water to obtain a transparent or quasi-transparent product of high viscosity containing from 15% to 30% weight by weight of the salified product of hydrolyzed jojoba oil.

iv) Self-emulsified jojoba oil (SEJO) comprising an emulsion from 1% to 40% weight by weight of jojoba oil in HJO obtained by treating the fatty acids with tromethamine in ethanol and dispersed in a sufficient amount of water to obtain a transparent or quasi-transparent product of high viscosity containing from 15% to 30% weight by weight of the salified product of hydrolyzed jojoba oil.

v) Self-emulsified jojoba oil (SEJO) comprising an emulsion from 1% to 40% weight by weight of jojoba oil in HJO obtained by treating the fatty acids with triethanolamine in propylene glycol and dispersed in a sufficient amount of water to obtain a transparent or quasi-transparent product of high viscosity containing from 15% to 30% weight by weight of the salified product of hydrolyzed jojoba oil.

vi) Self-emulsified jojoba oil (SEJO) comprising an emulsion from 1% to 40% weight by weight of jojoba oil in HJO obtained by treating the fatty acids with diethanolamine in propylene glycol and dispersed in a sufficient amount of water to obtain a transparent or quasi-transparent product of high viscosity containing from 15% to 30% weight by weight of the salified product of hydrolyzed jojoba oil.

vii) Self-emulsified jojoba oil (SEJO) comprising an emulsion from 1% to 40% weight by weight of jojoba oil in HJO obtained by treating the fatty acids with diethylamine in propylene glycol and dispersed in a sufficient amount of water to obtain a transparent or quasi-transparent product of high viscosity containing from 15% to 30% weight by weight of the salified product of hydrolyzed jojoba oil.

viii) Self-emulsified jojoba oil (SEJO) comprising an emulsion from 1% to 40% weight by weight of jojoba oil in HJO obtained by treating the fatty acids with tromethamine in propylene glycol and dispersed in a sufficient amount of water to obtain a transparent or quasi-transparent product of high viscosity containing from 15% to 30% weight by weight of the salified product of hydrolyzed jojoba oil.

ix) Self-emulsified jojoba oil (SEJO) comprising an emulsion from 1% to 40% weight by weight of jojoba oil in HJO obtained by treating the fatty acids with triethanolamine in a mixture of ethanol and propylene glycol and dispersed in a sufficient amount of water to obtain a transparent or quasi-transparent product of high viscosity containing from 15% to 30% weight by weight of the salified product of hydrolyzed jojoba oil.

x) Self-emulsified jojoba oil (SEJO) comprising an emulsion from 1% to 40% weight by weight of jojoba oil in HJO obtained by treating the fatty acids with diethanolamine in a mixture of ethanol and propylene glycol and dispersed in a sufficient amount of water to obtain a transparent or quasi-transparent product of high viscosity containing from 15% to 30% weight by weight of the salified product of hydrolyzed jojoba oil.

xi) Self-emulsified jojoba oil (SEJO) comprising an emulsion from 1% to 40% weight by weight of jojoba oil in HJO obtained by treating the fatty acids with diethylamine in a mixture of ethanol and propylene glycol and dispersed in a sufficient amount of water to obtain a transparent or quasi-transparent product of high viscosity containing from 15% to 30% weight by weight of the salified product of hydrolyzed jojoba oil.

xii) Self-emulsified jojoba oil (SEJO) comprising an emulsion from 1% to 40% weight by weight of jojoba oil in HJO obtained by treating the fatty acids with tromethamine in a mixture of ethanol and propylene glycol and dispersed in a sufficient amount of water to obtain a transparent or quasi-transparent product of high viscosity containing from 15% to 30% weight by weight of the salified product of hydrolyzed jojoba oil.

III) From the HJO described in I) transparent or translucent dispersions of an NSAID, wherein the NSAID is added to the HJO in a concentration from 0.1% to 1%; and wherein preferred NSAID are: ketoprofen, ibuprofen, naproxen, flurbiprofen, diclofenac, indomethacin and piroxicam.

Therefore, each of the twelve hydrolyzed jojoba oils (HJO) described in I) can be utilized to carry an NSAID, thus obtaining a pharmaceutical composition.

IV) From several HJO described in I) opaque dispersions of antiviral agents may be obtained, wherein an antiviral agent is added to the HJO in a concentration from 0.5% to 5%; and wherein preferred antiviral agent are: acyclovir, penciclovir, idoxuridine.

Therefore, each of the twelve hydrolyzed jojoba oils (HJO) described in I) can be utilized to disperse an antiviral agent, thus obtaining a pharmaceutical composition.

V) From several HJO described in I) transparent or translucent dispersions of local anesthetic drugs comprising 0.5% to 5% of a local anesthetic agent in the HJO; and wherein preferred local anesthetics agents are: lidocaine, benzocaine, tetracaine or procaine.

Therefore, each of the twelve hydrolyzed jojoba oils (HJO) described in I) can be utilized to dissolve a local anesthetic agent, thus obtaining a pharmaceutical composition.

VI) From several self-emulsified jojoba oils (SEJO) described in II) useful for skin care it is possible to obtain new cosmetic products as a result of their ability to carry liposoluble vitamins, preferably vitamins A, D, and E, and hydro soluble vitamins, preferably vitamin C, as well as other cosmetic active principles.

EXAMPLES

Example 1

Obtaining an Aqueous Dispersion of Alcohols and Acids of Hydrolyzed Jojoba Oil (HJO)

1) In a multi-neck round-bottom flask equipped with a condenser, magnetic stirring and a thermostatic bath at 60° C., was heated under reflux, 2.6 g of sodium hydroxide in 200 ml of a solution of methyl alcohol/$H_2O$ (99:1), until dissolution. Further 20 g of jojoba oil was added to this solution, and boiled for one hour and 30 minutes.

2) The product of the hydrolysis was recovered through evaporation of the solvent at reduced pressure obtaining a solid, which at a temperature higher than 25° C. is a light yellowish semisolid product. Adding to the semisolid product 35 ml of water while stirring, 35 ml of 2 N hydrochloric acid solution, the product obtained was placed in a cool place during 24 hours.

3) The aqueous phase was separated by decantation and the resulting product was washed with 100 ml of distilled water each time until the absence of chlorides in the washing liquids was verified with silver nitrate.

4) This semisolid product at room temperature was dissolved in a solution comprising 2.5 ml of triethanolamine in 22 ml of ethyl alcohol. A homogeneous and stable solution of intense gold color, called "solution of hydrolyzed jojoba oil," was obtained.

5) Afterwards, the solution obtained was mixed with water, with gentle stirring to incorporate the phases completely thus obtaining a high-viscosity, transparent gel containing from 15% to 30% of the mixture of alcohols and salified acids of jojoba named hydrolyzed jojoba oil (HJO).

Figure 2:
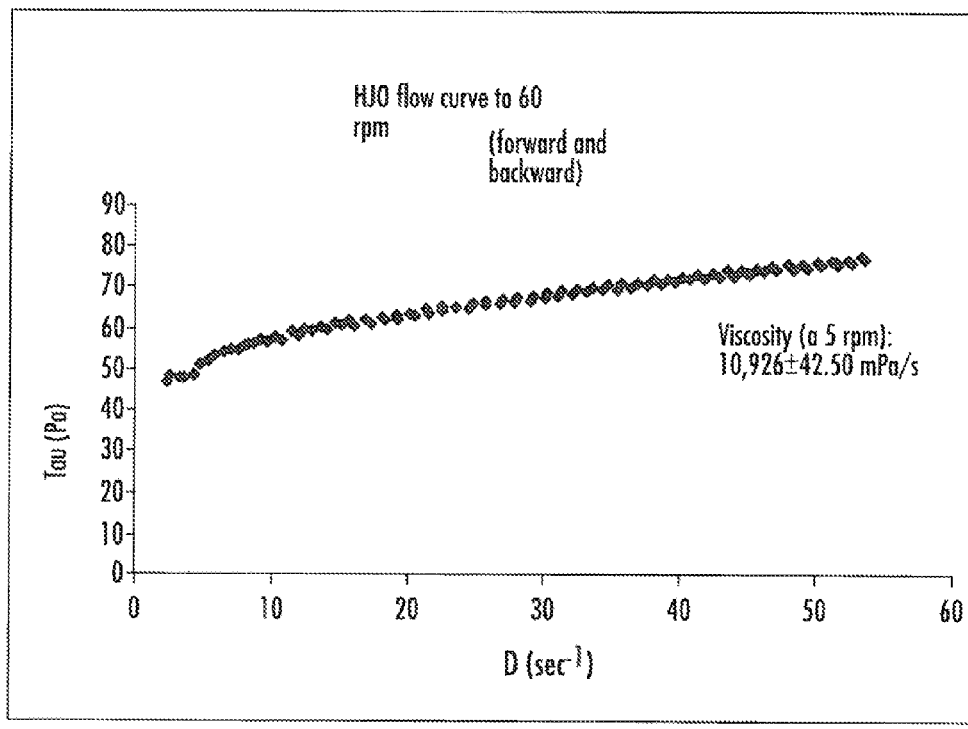
FIG. 2 shows the rheological behavior of the hydrolyzed jojoba oil product (WO), by a flow curve up to 60 rpm generated forward and backward at 25° C.

FIG. 2 shows the rheological behavior of the hydrolyzed jojoba oil (HJO), by a flow curve from 0 to 60 rpm generated forward and backward at 25° C.

Figure 3:
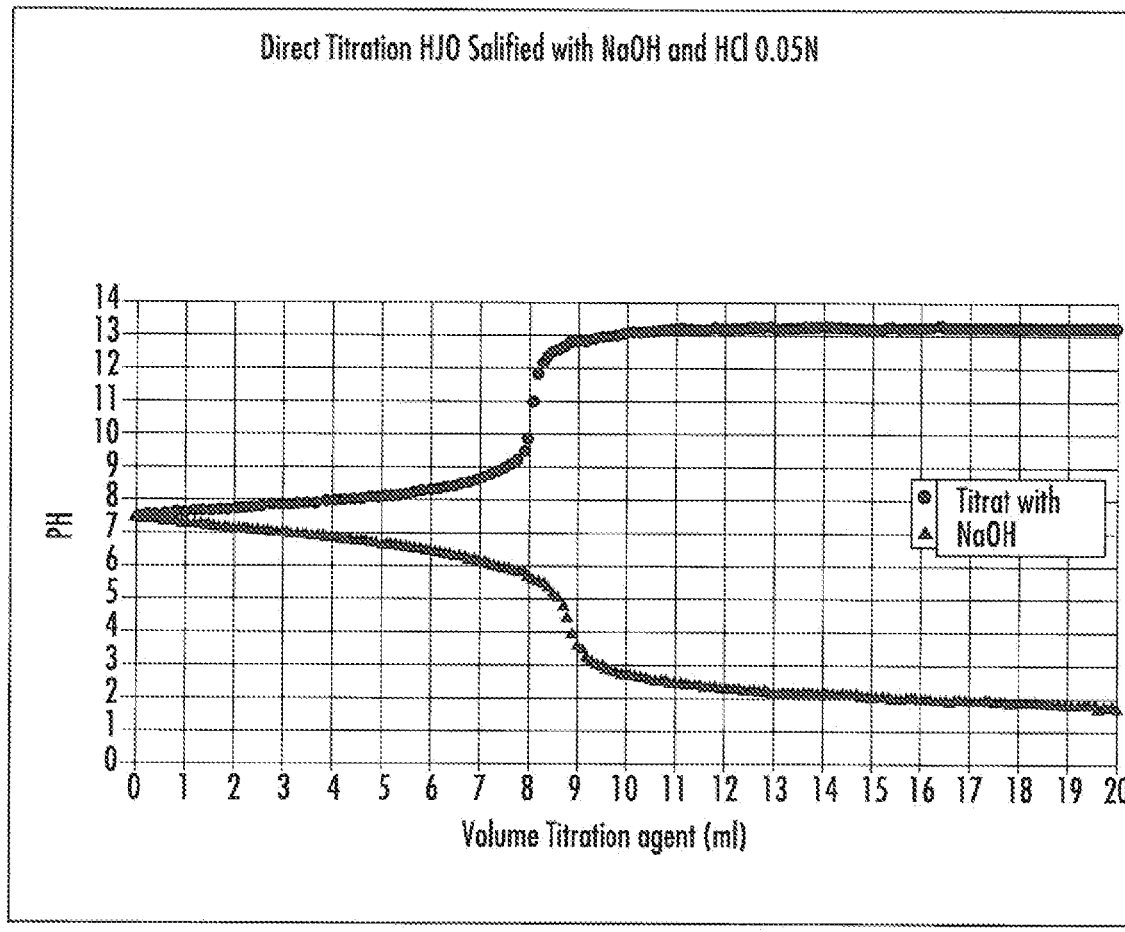
FIG. 3 shows analytical controls of the hydrolyzed jojoba oil product (HJO) by a titration curve of HJO with NaOH 0.05 N and with HCl 0.05 N.

FIG. 3 shows the neutralization level of carboxylic acids of jojoba oil, obtained by titration of HJO with NaOH 0.05 N and HCl 0.05 N

Example 2

Obtaining a Transparent or Translucent Dispersion of Diclofenac at a Concentration of 1% in an Aqueous Dispersion of Alcohols and Acids of Hydrolyzed Jojoba Oil (HJO)

To 50 ml of the solution of hydrolyzed jojoba oil obtained as described, in step 4, of Example 1, 1.00 g of Diclofenac was added under stirring, the mixture was warmed up to 40° C. to complete the solid's dissolution. 50 ml of water was slowly poured into the mixture while stirring to obtain a high-viscosity and transparent, homogeneous product.

Figure 4:
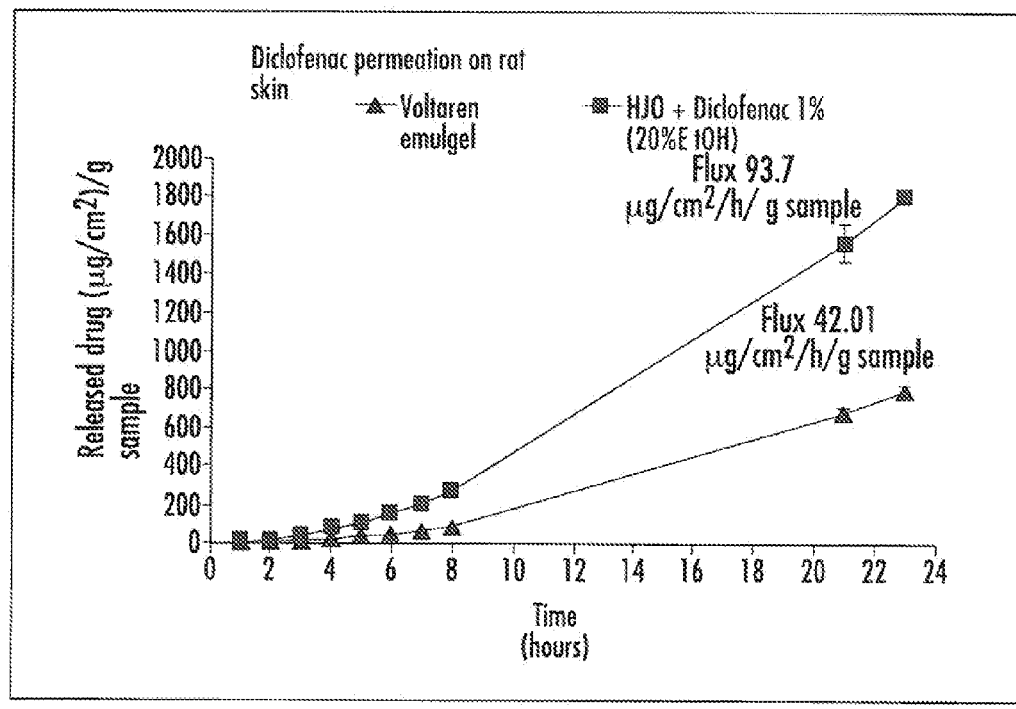
FIG. 4 refers to a rat skin permeation assay of Diclofenac 1% w/w in HJO, determined by HPLC, wherein the promoting effect of transdermal permeability of the product HJO is noted.

FIG. 4 shows the results obtained by HPLC of a permeation assay to the product (HJO+Diclofenac 1% w/w) in rat skin, emphasizing the transdermal permeation promoting effect of the product.

Example 3

Obtaining an Opaque Dispersion of the Antiviral Acyclovir at a Concentration of 5% in an Aqueous Dispersion of Alcohols and Salified Acids of Hydrolyzed Jojoba Oil (HJO)

To 50 ml of hydrolyzed jojoba oil obtained as described in step 4, of Example 1, 5 g of Acyclovir as finely divided powder was slowly added while stirring to obtain a homogeneous dispersion. Then, 50 ml of water was slowly poured into the mixture while stirring to obtain an opaque semisolid product of fine texture and bright white color.

Figure 5:
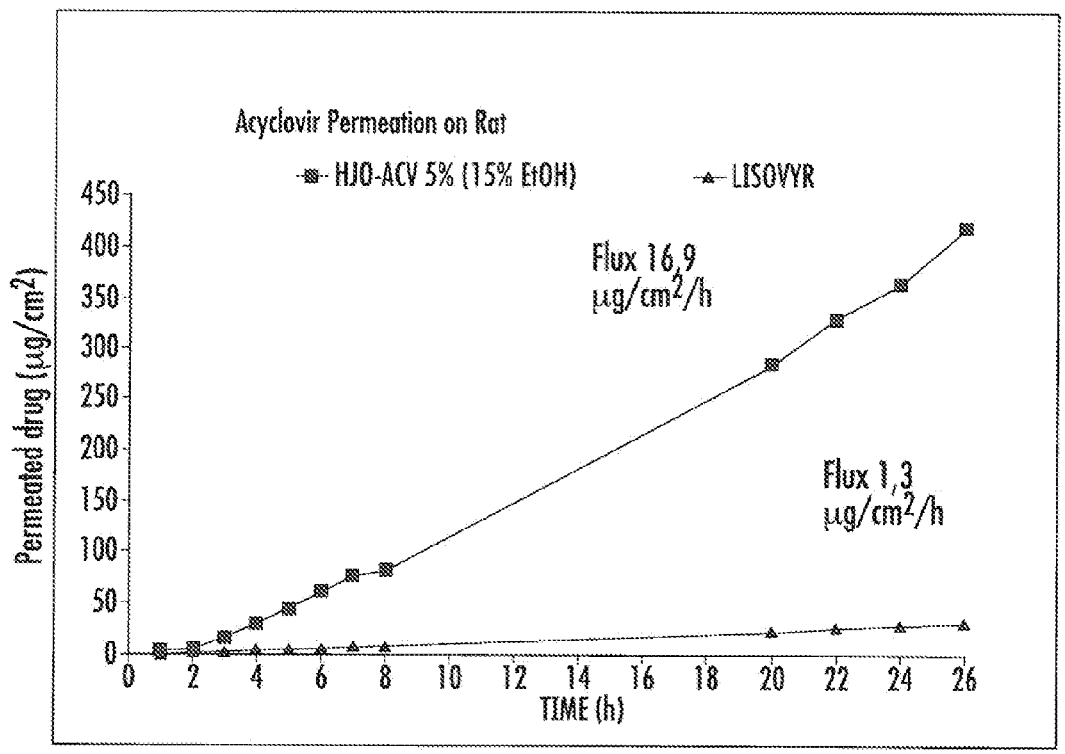
FIG. 5 refers to a rat skin permeation assay of Acyclovir 5% w/w in HJO, determined by HPLC, wherein the promoting effect of transdermal permeability of the product HJO is noted.

FIG. 5 shows the results obtained by HPLC of a permeation assay to the product (HJO+Aciclovir 5% w/w) in rat skin, emphasizing the transdermal permeation promoting effect of the product.

Example 4

Obtaining Self-Emulsified Jojoba Oil (SEJO)

Procedure A)

17.7 g of jojoba oil was added to 100 g of HJO while vigorously mixing to form a homogeneous, high-viscosity, brightly textured semisolid product. The SEJO obtained contains jojoba oil at a ratio of 15% w/w.

Procedure B)

17.7 g of jojoba oil was added to 55 ml of hydrolyzed jojoba oil solution obtained according to step 4 of Example 1, gently stirring the mixture until completing the incorporation of the phases. To this solution 55 ml of $H_2O$ was added slowly under stirring to form a homogeneous, high-viscosity and brightly textured semisolid product. The SEJO obtained contains jojoba oil at a ratio of 15% w/w.

Example 5

Obtaining a Cream with Vitamin A for Damaged Skin, from Self-Emulsified Jojoba Oil (SEJO)

A solution containing 600,000 IU of vitamin A Palmitate in 17.7 g of jojoba oil was added to 55 ml of hydrolyzed jojoba oil solution obtained as described in step 4 of Example 1, and the mixture was gently stirred until the complete incorporation of the phases. To this solution was dropped 55 ml of water under stirring to form a homogeneous, high-viscosity brightly textured semisolid product. The SEJO obtained contains 15% w/w of jojoba oil and 600,000 IU of vitamin A palmitate.

Therefore the above descriptions should not be construed as limiting, but merely as exemplifications of preferred embodiments.

What is claimed is:

1. A process for obtaining an aqueous dispersion of alcohols and acids from jojoba oil useful as a vehicle for pharmaceutical and cosmetic compositions, comprising the steps of:
   a) saponifying jojoba oil esters (I) by a base (II) to produce a mixture of carboxylates of formula (III) and jojoba alcohols of formula (IV), according to the following reaction:

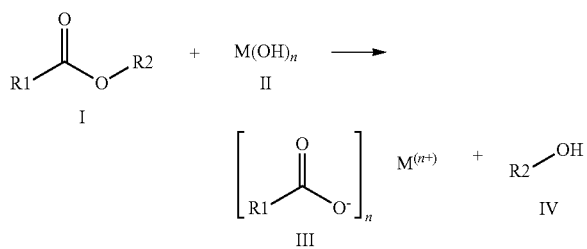

wherein: R1, R2 are alkenes of C20-C22; M are alkali metals or alkali earth metals and n is 1 or 2 in a reaction medium comprising a solvent, wherein the solvent comprises a solution of methyl alcohol and water at boiling temperature;
   b) evaporating the solvent to dryness by means of reduced pressure to obtain a product;
   c) adding to the product obtained in step b) an aqueous solution of a strong inorganic acid or of an organic acid, thus obtaining a solid or semisolid product comprising a mixture of fatty acids and alcohols of jojoba oil in an aqueous medium;
   d) separating the solid or semisolid product from the aqueous medium;
   e) salifying the fatty acids of the solid or semisolid product separated in step d) by adding an aliphatic amine previously dissolved in a suitable volume of a co-solvent to obtain a product; and
   f) dispersing the product of step e) in a sufficient amount of water to obtain a transparent or quasi-transparent high-viscosity product.

2. The process of claim 1, wherein step c) is conducted before step b), acidifying the reaction product before separating the solvent.

3. The process of claim 1, wherein the base is sodium hydroxide or potassium hydroxide, and the solution of methyl alcohol and water is at a ratio of 99:1 and the temperature ranges from 60° C. to 70° C.

4. The process of claim 1, wherein the strong inorganic acid is hydrochloric acid at concentrations of 1% to 30% w/v.

5. The process of claim 1, wherein the aliphatic amine is selected from the group consisting of dialkyl ($C_1$-$C_6$) amines, dihydroxyalkyl ($C_1$-$C_6$) amines, trihydroxyalkyl ($C_1$-$C_6$) amines, and mixtures thereof.

6. The process of claim 1, wherein a sufficient amount of the aliphatic amine is previously dissolved in a suitable volume of a co-solvent to obtain a concentration of co-solvent in the final product from 15% to 25% w/w.

7. The process of claim 6, wherein the co-solvent is selected from the group consisting of ethyl alcohol, propylene glycol, and mixtures thereof.

8. The process of claim 1, wherein salifying the fatty acids by adding an aliphatic amine is carried out from 50% to 100% of the number of existing carboxylic groups.

9. The procedure of claim 1, wherein the transparent or quasi-transparent high-viscosity product obtained in step f) contains from 15% to 30% w/w of the salified product of hydrolysis of jojoba oil, named Hydrolyzed Jojoba Oil (HJO).

10. A process for obtaining self-emulsified jojoba oil (SEJO) comprising:
   a) combining jojoba oil with the transparent or quasi-transparent high-viscosity product obtained by the process of claim 1 to obtain a mixture; and
   b) vigorously stirring the mixture to obtain a self-emulsified jojoba oil (SEJO) as a semisolid, homogeneous, brightly textured product.

11. A process for obtaining self-emulsified jojoba oil (SEJO) comprising jojoba oil dispersed in an aqueous dispersion of alcohols and salified fatty acids of hydrolyzed jojoba oil (HJO), wherein said process comprises:
   a) adding jojoba oil to a solution of the product of salified fatty acids obtained in step e) of the process of claim 1 to obtain a mixture;
   b) gently stirring the mixture until completing the incorporation of the phases; and
   c) adding water slowly while stirring, until obtaining a semisolid, homogeneous, high-viscosity, brightly textured product.

12. The process of claim 10, wherein the self-emulsified jojoba oil (SEJO) contains from 1% to 40% of jojoba oil dispersed in the product of the aqueous dispersion of alcohols and salified acids from hydrolysed jojoba oil (HJO).

13. The process of claim 1, wherein the co-solvent in step e) is ethanol or propylene glycol.

14. The process of claim 5, wherein the aliphatic amine is triethanolamine, diethanolamine, tromethamine, diethylamine, or a mixture thereof.

15. The process of claim 12, wherein the SEJO contains 15% of jojoba oil dispersed in the product of the aqueous dispersion of alcohols and salified acids from hydrolyzed jojoba oil (HJO).

* * * * *